US012390196B2

(12) United States Patent
Yin et al.

(10) Patent No.: US 12,390,196 B2
(45) Date of Patent: Aug. 19, 2025

(54) IMAGE PROCESSING METHOD AND APPARATUS BASED ON CONTRAST-ENHANCED ULTRASOUND IMAGES TO IMPROVE SPATIAL SPARSITY OF MICROBUBBLES

(71) Applicant: Nanjing Leapsonics Technology Co., Ltd., Nanjing (CN)

(72) Inventors: Jingyi Yin, Nanjing (CN); Jue Zhang, Nanjing (CN)

(73) Assignee: Nanjing Leapsonics Technology Co., Ltd., Nanjing (CN)

( * ) Notice: Subject to any disclaimer, the term of this patent is extended or adjusted under 35 U.S.C. 154(b) by 741 days.

(21) Appl. No.: 17/838,106

(22) Filed: Jun. 10, 2022

(65) Prior Publication Data
US 2022/0296216 A1 Sep. 22, 2022

Related U.S. Application Data

(63) Continuation of application No. PCT/CN2021/093474, filed on May 13, 2021.

(30) Foreign Application Priority Data

May 18, 2020 (CN) .......................... 202010419611.5

(51) Int. Cl.
*A61B 8/00* (2006.01)
*A61B 8/08* (2006.01)
(52) U.S. Cl.
CPC ............ *A61B 8/481* (2013.01); *A61B 8/0891* (2013.01); *G06T 2207/10136* (2013.01)
(58) Field of Classification Search
CPC ....... A61B 8/481; A61B 8/0891; A61B 8/483; A61B 8/5207; A61B 8/5223; A61B 8/5238; G06T 2207/10136
See application file for complete search history.

(56) References Cited

U.S. PATENT DOCUMENTS

2015/0196279 A1   7/2015   Ketterling et al.

FOREIGN PATENT DOCUMENTS

CN   103006272 A   4/2013
CN   108324324 A   7/2018
(Continued)

OTHER PUBLICATIONS

Ackermann et al., Detection and Tracking of Multiple Microbubbles in Ultrasound B-Mode Images, IEEE Transactions on Ultrasonics, Ferroelectrics, and Frequency Control, vol. 63, No. 1, pp. 72-82, dated Jan. 2, 2016.
(Continued)

*Primary Examiner* — Serkan Akar
(74) *Attorney, Agent, or Firm* — Westbridge IP LLC

(57) ABSTRACT

Disclosed are an image processing method and an apparatus based on contrast-enhanced ultrasound images, a computer readable storage medium and an electronic device. The image processing method based on contrast-enhanced ultrasound images includes: performing a first decoupling operation on a first contrast-enhanced ultrasound image sequence to generate a second contrast-enhanced ultrasound image sequence corresponding to the first contrast-enhanced ultrasound image sequence, the first decoupling operation being used to improve spatial sparsity of microbubbles; and performing a second decoupling operation on the second contrast-enhanced ultrasound image sequence to generate a third contrast-enhanced ultrasound image sequence corresponding to the second contrast-enhanced ultrasound image sequence, the second decoupling operation being used to improve temporal sparsity of the microbubbles. The image processing method based on contrast-enhanced ultrasound images not only improve a signal-to-noise ratio of a contrast-enhanced ultrasound image sequence, but also (Continued)

improves a degree of spatial-temporal sparsity of the microbubbles.

17 Claims, 9 Drawing Sheets

(56) References Cited

FOREIGN PATENT DOCUMENTS

| | | | |
|---|---|---|---|
| CN | 108882914 | A | 11/2018 |
| CN | 110772285 | A | 2/2020 |
| CN | 111588410 | A | 8/2020 |
| WO | 2018222724 | A1 | 12/2018 |

OTHER PUBLICATIONS

Extended European Search Report issued in counterpart European Patent Application No. 21808103.2, dated Jan. 11, 2023.
Song et al., Improved Super-Resolution Ultrasound Microvessel Imaging With Spatiotemporal Nonlocal Means Filtering and Bipartite Graph-Based Microbubble Tracking, IEEE Transactions on Ultrasonics, Ferroelectrics, and Frequency Control, vol. 65, No. 2, pp. 149-167, dated Feb. 2, 2018.
Written Opinion issued in corresponding PCT Application No. PCT/CN2021/093474, dated Aug. 13, 2021.
International Search Report issued in corresponding PCT Application No. PCT/CN2021/093474, dated Aug. 13, 2021.

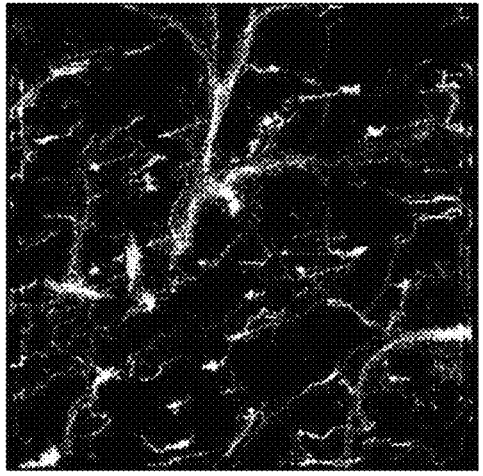 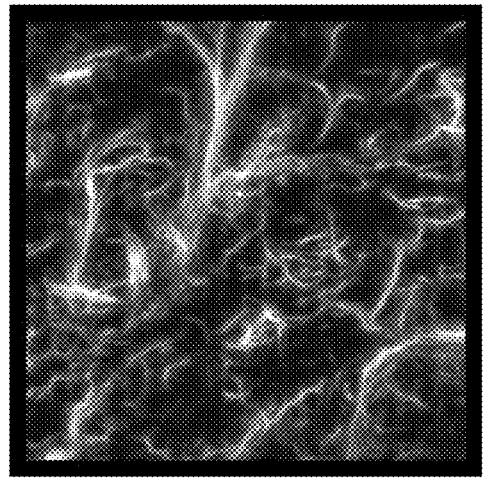
FIG. 4a                    FIG. 4b
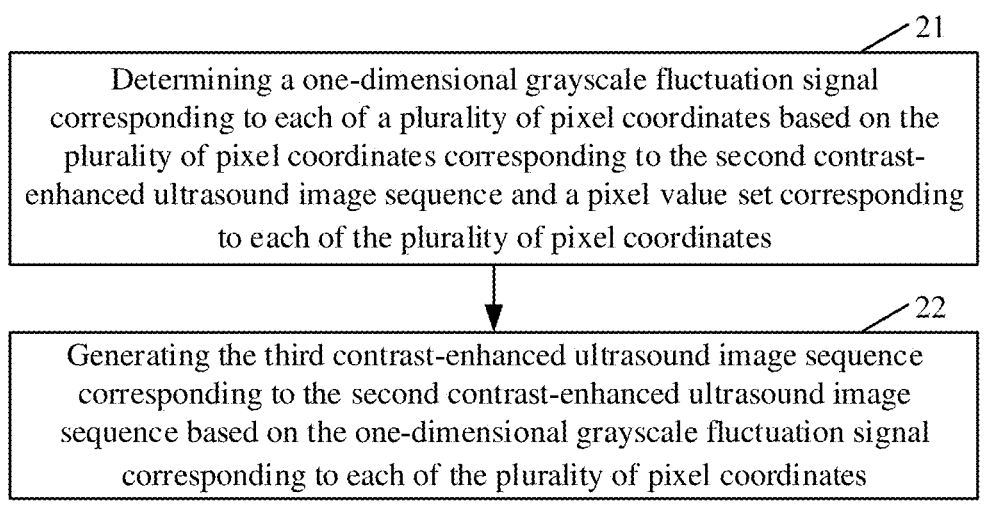
FIG. 5

IMAGE PROCESSING METHOD AND APPARATUS BASED ON CONTRAST-ENHANCED ULTRASOUND IMAGES TO IMPROVE SPATIAL SPARSITY OF MICROBUBBLES

CROSS-REFERENCE TO RELATED APPLICATIONS

The present application is a continuation of International Application No. PCT/CN2021/093474, filed on May 13, 2021, which claims priority to Chinese Patent Application No. 202010419611.5, filed on May 18, 2020. All applications are incorporated herein by reference in their entireties.

TECHNICAL FIELD

The present application relates to the field of image processing technologies, in particular to an image processing method and an apparatus based on contrast-enhanced ultrasound images, a non-transitory computer readable storage medium and an electronic device.

BACKGROUND

Ultrasound Localization Microscopy (ULM) mainly achieves a purpose of microvascular imaging by localizing isolated microbubble signals. Therefore, an influence of acoustic diffraction limit may be overcome by using ULM, and importance of ULM is self-evident.

However, high concentration microbubbles may affect the accuracy of microbubble localization process, and microbubbles in deeper tissues are susceptible to interference from tissue motion (such as soft tissue motion due to cardiac beating). Therefore, in the prior art, the precision of microbubble localization is poor under clinical settings.

SUMMARY

In order to solve the above technical problems, an image processing method and an apparatus based on contrast-enhanced ultrasound images, a non-transitory computer readable storage medium and an electronic device are provided according to embodiments of the present application.

According to an aspect, an embodiment of the present application provides an image processing method based on contrast-enhanced ultrasound images, applied to a first contrast-enhanced ultrasound image sequence including microbubbles. The image processing method based on contrast-enhanced ultrasound images includes: performing a first decoupling operation on the first contrast-enhanced ultrasound image sequence to generate a second contrast-enhanced ultrasound image sequence corresponding to the first contrast-enhanced ultrasound image sequence, the first decoupling operation being used to improve spatial sparsity of the microbubbles; and performing a second decoupling operation on the second contrast-enhanced ultrasound image sequence to generate a third contrast-enhanced ultrasound image sequence corresponding to the second contrast-enhanced ultrasound image sequence, the second decoupling operation being used to improve temporal sparsity of the microbubbles.

According to an embodiment of the present application, the performing a second decoupling operation on the second contrast-enhanced ultrasound image sequence to generate a third contrast-enhanced ultrasound image sequence corresponding to the second contrast-enhanced ultrasound image sequence includes: determining one-dimensional grayscale fluctuation signals corresponding to a plurality of pixel coordinates respectively, based on the plurality of pixel coordinates corresponding to the second contrast-enhanced ultrasound image sequence and pixel value sets corresponding to the plurality of pixel coordinates respectively; and generating the third contrast-enhanced ultrasound image sequence corresponding to the second contrast-enhanced ultrasound image sequence based on the one-dimensional grayscale fluctuation signals corresponding to the plurality of pixel coordinates respectively.

According to an embodiment of the present application, the generating the third contrast-enhanced ultrasound image sequence corresponding to the second contrast-enhanced ultrasound image sequence based on the one-dimensional grayscale fluctuation signals corresponding to the plurality of pixel coordinates respectively includes: performing a multi-scale decomposition operation on the one-dimensional grayscale fluctuation signals corresponding to the plurality of pixel coordinates to generate first multi-scale decomposition signal sets corresponding to the plurality of pixel coordinates respectively; performing, for each pixel coordinate in the plurality of pixel coordinates, a filtering operation on the first multi-scale decomposition signal set corresponding to the pixel coordinate to generate a second multi-scale decomposition signal set corresponding to the pixel coordinate, the filtering operation being used to filter out a decomposition signal of a preset scale in the first multi-scale decomposition signal set; performing a splicing operation on the second multi-scale decomposition signal set corresponding to the pixel coordinate to generate a splicing signal corresponding to the pixel coordinate; and generating the third contrast-enhanced ultrasound image sequence corresponding to the second contrast-enhanced ultrasound image sequence based on splicing signals corresponding to the plurality of pixel coordinates respectively.

According to an embodiment of the present application, the decomposition signal of the preset scale includes a decomposition signal with a smallest scale in the first multi-scale decomposition signal set.

According to an embodiment of the present application, before the determining one-dimensional grayscale fluctuation signals corresponding to a plurality of pixel coordinates respectively, based on the plurality of pixel coordinates corresponding to the second contrast-enhanced ultrasound image sequence and pixel value sets corresponding to the plurality of pixel coordinates respectively, the image processing method further includes: determining a space coordinate system corresponding to the second contrast-enhanced ultrasound image sequence, the space coordinate system being capable to represent image sequence information; and determining the plurality of pixel coordinates corresponding to the second contrast-enhanced ultrasound image sequence and the pixel value sets corresponding to the plurality of pixel coordinates respectively, based on the second contrast-enhanced ultrasound image sequence and the spatial coordinate system.

According to an embodiment of the present application, the determining one-dimensional grayscale fluctuation signals corresponding to a plurality of pixel coordinates respectively, based on the plurality of pixel coordinates corresponding to the second contrast-enhanced ultrasound image sequence and pixel value sets corresponding to the plurality of pixel coordinates respectively includes: splicing, for each pixel coordinate in the plurality of pixel coordinates, the pixel value set corresponding to the pixel coordinate into the one-dimensional grayscale fluctuation signal based on image sequence information represented by a spatial coordinate system, so as to determine the one-dimensional grayscale fluctuation signals corresponding to the plurality of pixel coordinates respectively.

According to an embodiment of the present application, the performing a first decoupling operation on the first contrast-enhanced ultrasound image sequence to generate a second contrast-enhanced ultrasound image sequence corresponding to the first contrast-enhanced ultrasound image sequence includes: determining, for each contrast-enhanced ultrasound image in the first contrast-enhanced ultrasound image sequence, distance information between a microbubble region in the contrast-enhanced ultrasound image and a background region corresponding to the microbubble region; performing a pixel weighting operation on the contrast-enhanced ultrasound image based on the distance information corresponding to the contrast-enhanced ultrasound image to generate a weighted image corresponding to the contrast-enhanced ultrasound image; and generating the second contrast-enhanced ultrasound image sequence corresponding to the first contrast-enhanced ultrasound image sequence based on weighted images respectively corresponding to contrast-enhanced ultrasound images of the first contrast-enhanced ultrasound image sequence.

According to an embodiment of the present application, the determining distance information between a microbubble region in the contrast-enhanced ultrasound image and a background region corresponding to the microbubble region includes: performing a binarization processing on the contrast-enhanced ultrasound image based on the microbubble region and the background region to generate a binarized image; and determining the distance information between the microbubble region and the background region based on the binarized image.

According to an embodiment of the present application, the microbubble region includes a plurality of pixel blocks, and the determining distance information between a microbubble region in the contrast-enhanced ultrasound image and a background region corresponding to the microbubble region includes: determining, for each pixel block of the plurality of pixel blocks, a shortest distance from the pixel block to the background region; and determining the distance information based on shortest distances respectively corresponding to the plurality of pixel blocks.

According to another aspect, an embodiment of the present application provides an image processing apparatus based on contrast-enhanced ultrasound images, applied to a first contrast-enhanced ultrasound image sequence including microbubbles. The image processing apparatus based on contrast-enhanced ultrasound images includes a memory, a processor, and a computer program stored in the memory and executed by the processor, wherein when the computer program is executed by the processor, the processor implements the following steps: performing a first decoupling operation on the first contrast-enhanced ultrasound image sequence to generate a second contrast-enhanced ultrasound image sequence corresponding to the first contrast-enhanced ultrasound image sequence, the first decoupling operation being used to improve spatial sparsity of the microbubbles; and performing a second decoupling operation on the second contrast-enhanced ultrasound image sequence to generate a third contrast-enhanced ultrasound image sequence corresponding to the second contrast-enhanced ultrasound image sequence, the second decoupling operation being used to improve temporal sparsity of the microbubbles.

According to another aspect, an embodiment of the present application provides a non-transitory computer readable storage medium storing a computer program for executing the image processing method based on contrast-enhanced ultrasound images according to any one of the above embodiments.

According to another aspect, an embodiment of the present application provides an electronic device. The electronic device including: a processor; and a memory for storing instructions executable by the processor. The processor is configured to execute the image processing method based on contrast-enhanced ultrasound images according to any one of the above embodiments.

The image processing method based on contrast-enhanced ultrasound images according to embodiments of the present application, by performing a first decoupling operation and a second decoupling operation on a first contrast-enhanced ultrasound image sequence respectively, not only improves a signal-to-noise ratio of a contrast-enhanced ultrasound image sequence, but also improves a degree of spatial-temporal sparsity (including the temporal sparsity and the spatial sparsity) of the microbubbles, thereby breaking limitation of a microbubble concentration in existing microbubble localization methods, and further providing a prerequisite for improving accuracy of locating the microbubbles. In addition, the embodiments of the present application effectively solve problems of the microbubble concentration and background noise in a clinical application scene, thereby providing favorable conditions for improving speed and accuracy of subsequent super-resolution image reconstruction.

BRIEF DESCRIPTION OF THE DRAWINGS

The above and other objects, features and advantages of the present application will become more obvious from the detailed description of the embodiments of the present application in conjunction with the accompanying drawings. The accompanying drawings are used to provide a further understanding of the embodiments of the present application, constitute a part of the specification, and are used to explain the present application together with the embodiments of the present application, and do not constitute a limitation to the present application. In the accompanying drawings, the same reference numbers generally refer to the same components or steps.

FIG. 4*a* and FIG. 4*b* are schematic diagrams of super-resolution reconstruction corresponding to a contrast-enhanced ultrasound image sequence.

FIG. 5 is a schematic flowchart of performing a second decoupling operation on the second contrast-enhanced ultrasound image sequence to generate a third contrast-enhanced ultrasound image sequence corresponding to the second contrast-enhanced ultrasound image sequence according to an exemplary embodiment of the present application.

DETAILED DESCRIPTION OF THE EMBODIMENTS

Exemplary embodiments according to the present application will be described in detail below with reference to the accompanying drawings. Obviously, the described embodiments are only a part of the embodiments of the present disclosure, not all of the embodiments. It should be understood that the present application is not limited by the exemplary embodiments described herein.

Figure 1:
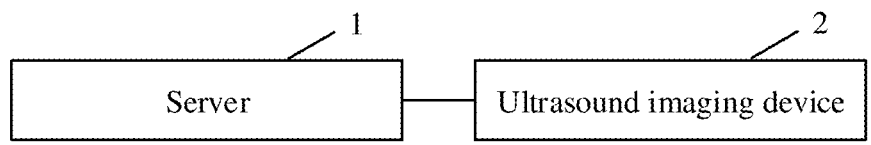
FIG. 1 is a schematic diagram of a scene applicable to an embodiment of the present application.

FIG. 1 is a schematic diagram of a scene applicable to an embodiment of the present application. As shown in FIG. 1, a scene applicable to an embodiment of the present application includes a server 1 and an ultrasound imaging device 2. There is a communication connection relationship between the server 1 and the ultrasound imaging device 2.

Specifically, the ultrasound imaging device 2 is configured to acquire a first contrast-enhanced ultrasound image sequence including microbubbles. The server 1 is configured to perform a first decoupling operation on the first contrast-enhanced ultrasound image sequence to generate a second contrast-enhanced ultrasound image sequence corresponding to the first contrast-enhanced ultrasound image sequence, the first decoupling operation being used to improve spatial sparsity of the microbubbles; and perform a second decoupling operation on the second contrast-enhanced ultrasound image sequence to generate a third contrast-enhanced ultrasound image sequence corresponding to the second contrast-enhanced ultrasound image sequence, the second decoupling operation being used to improve temporal sparsity of the microbubbles. That is, the scene realizes an image processing method based on contrast-enhanced ultrasound images.

Since the above scene shown in FIG. 1 realizes, by the server 1, the image processing method based on the contrast-enhanced ultrasound images, not only adaptability of the scene is improved, but also calculation procedure of the ultrasound imaging device 2 is effectively reduced.

Figure 2:
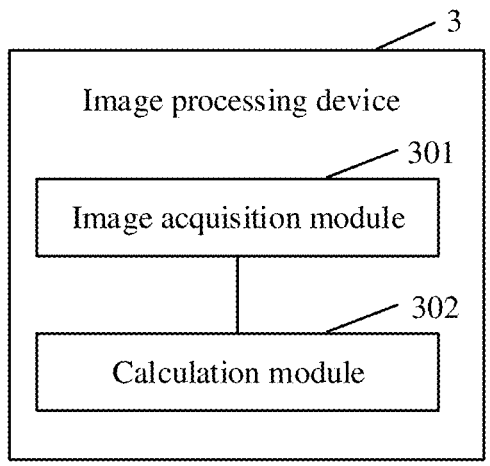
FIG. 2 is a schematic diagram of another scene applicable to an embodiment of the present application.

The present disclosure also applies to another scene. FIG. 2 is a schematic diagram of another scene applicable to an embodiment of the present application. Specifically, the scene includes an image processing device 3, and the image processing device 3 includes an image acquisition module 301 and a calculation module 302. There is a communication connection between the image acquisition module 301 and the calculation module 302.

Specifically, the image acquisition module 301 in the image processing device 3 may be configured to perform functions of the ultrasound imaging device 2 in the scene shown in FIG. 1. The calculation module 302 in the image processing device 3 may be configured to perform functions of the server 1 in the scene shown in FIG. 1. Repetition is not included here in the embodiments of the present application.

Since the above scene shown in FIG. 2 realizes, by the image processing device 3, the image processing method based on contrast-enhanced ultrasound images, and there is no need to perform data transmission operations with related devices such as servers, the above scene shown in FIG. 2 may ensure real-time performance of the image processing method based on contrast-enhanced ultrasound images.

Figure 3:
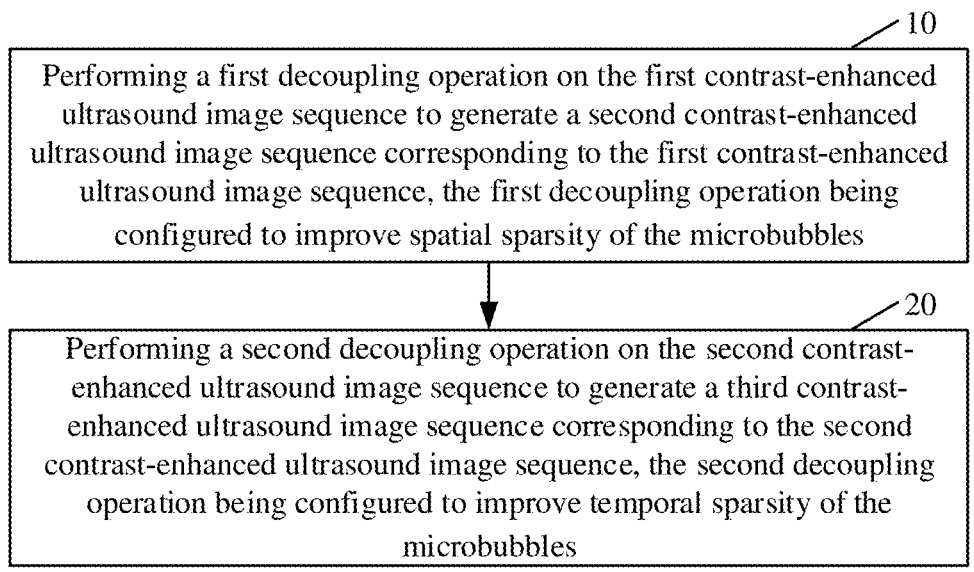
FIG. 3 is a schematic flowchart of an image processing method based on contrast-enhanced ultrasound images according to an exemplary embodiment of the present application.

FIG. 3 is a schematic flowchart of an image processing method based on contrast-enhanced ultrasound images according to an exemplary embodiment of the present application. As shown in FIG. 3, the image processing method based on contrast-enhanced ultrasound images according to embodiments of the present application include the following steps.

Step 10, performing a first decoupling operation on the first contrast-enhanced ultrasound image sequence to generate a second contrast-enhanced ultrasound image sequence corresponding to the first contrast-enhanced ultrasound image sequence, the first decoupling operation being used to improve spatial sparsity of microbubbles.

Exemplarily, the first contrast-enhanced ultrasound image sequence mentioned in Step 10 is a two-dimensional contrast-enhanced ultrasound image sequence including microbubbles acquired by an ultrasound imaging device. That is, the first contrast-enhanced ultrasound image sequence includes a plurality of first contrast-enhanced ultrasound images, and each of the first contrast-enhanced ultrasound images includes a microbubble region.

Exemplarily, the first decoupling operation is realized by highlighting a central region of the microbubbles along microbubble trajectories, and the first decoupling operation may suppress noise in a background region. The microbubble region refers to an image region corresponding to the microbubbles in the first contrast-enhanced ultrasound image. The background region refers to a background image region that does not include the microbubbles in the first contrast-enhanced ultrasound image. Using the above-mentioned first decoupling operation to process the first contrast-enhanced ultrasound image sequence may not only effectively improve a signal-to-noise ratio of a contrast-enhanced ultrasound images, but also help to improve the spatial sparsity of the microbubbles (that is, a level of spatial sparsity), thereby providing a prerequisite for improving accuracy of microbubble localization process.

The above-mentioned spatial sparsity refers to sparsity among a plurality of microbubbles included in same contrast-enhanced ultrasound images.

According to an embodiment of the present application, a plurality of second contrast-enhanced ultrasound images included in the second contrast-enhanced ultrasound image sequence are obtained by performing the first decoupling operation on the plurality of first contrast-enhanced ultrasound images included in the first contrast-enhanced ultrasound image sequence one by one. For example, the first contrast-enhanced ultrasound image sequence is denoted as $S_R=\{S_R^j|j=1, 2, \ldots N\}$, the second contrast-enhanced ultrasound image sequence is denoted as $S_G=\{S_G^j|j=1, 2, \ldots N\}$.

Step 20, performing a second decoupling operation on the second contrast-enhanced ultrasound image sequence to generate a third contrast-enhanced ultrasound image sequence corresponding to the second contrast-enhanced ultrasound image sequence, the second decoupling operation being used to improve temporal sparsity of the microbubbles.

The embodiment of the present application does not limit a specific implementation manner of the second decoupling operation mentioned in Step 20, as long as the second decoupling operation can improve the temporal sparsity of the microbubbles, so as to provide a favorable condition for a subsequent microbubble locating operation and an ultrasound super-resolution reconstruction operation.

In a practical application process, first, the first decoupling operation is performed on the first contrast-enhanced ultrasound image sequence to generate the second contrast-enhanced ultrasound image sequence corresponding to the first contrast-enhanced ultrasound image sequence. Then, the second decoupling operation is performed on the second contrast-enhanced ultrasound image sequence to generate the third contrast-enhanced ultrasound image sequence corresponding to the second contrast-enhanced ultrasound image sequence.

The image processing method based on contrast-enhanced ultrasound images according to embodiments of the present application, by performing the first decoupling operation and the second decoupling operation on the first contrast-enhanced ultrasound image sequence respectively, not only improves the signal-to-noise ratio of a contrast-enhanced ultrasound image sequence, but also improves spatial-temporal sparsity (including the temporal sparsity and the spatial sparsity) of the microbubbles, thereby breaking a limitation of low microbubble concentration in existing ultrasound localization microscopy methods, and further providing a prerequisite for improving accuracy of microbubble localization. In addition, the embodiments of the present application effectively solve problems of the high microbubble concentration and background noise in a clinical application, thereby providing favorable conditions for improving speed and accuracy of subsequent super-resolution image reconstruction.

FIG. 4a and FIG. 4b are schematic diagrams of super-resolution reconstruction corresponding to a contrast-enhanced ultrasound image sequence. Specifically, original contrast-enhanced ultrasound image sequences corresponding to FIG. 4a and FIG. 4b are both contrast-enhanced ultrasound image sequences based on a lower extremity biceps blood vessels of a New Zealand white rabbit collected by an ultrasound imaging device. FIG. 4a is a schematic diagram of super-resolution reconstruction obtained by reconstructing the original contrast-enhanced ultrasound image sequence by using a widely-used ultrasound super-resolution imaging technology (such as ultrasound localization microscopy). FIG. 4b is a schematic diagram of super-resolution reconstruction obtained by processing and then reconstructing the original contrast-enhanced ultrasound image sequence using the image processing method based on contrast-enhanced ultrasound images according to an embodiment of the present application and the existing ultrasound localization microscopy.

As shown in FIG. 4a and FIG. 4b, an effect of a super-resolution reconstruction shown in FIG. 4b is significantly better than an effect of the super-resolution reconstruction shown in FIG. 4a. That is, the effect of the super-resolution reconstruction corresponding to the contrast-enhanced ultrasound image sequence obtained by processing the original contrast-enhanced ultrasound image sequence by using the image processing method based on contrast-enhanced ultrasound images according to the embodiment of the present application is better.

FIG. 5 is a schematic flowchart of performing a second decoupling operation on the second contrast-enhanced ultrasound image sequence to generate a third contrast-enhanced ultrasound image sequence corresponding to the second contrast-enhanced ultrasound image sequence according to an exemplary embodiment of the present application. The embodiment of the present application shown in FIG. 5 is extended based on the embodiment of the present application shown in FIG. 3. Differences between the embodiment shown in FIG. 5 and the embodiment shown in FIG. 3 are emphatically described below, and similarities may not be described repeatedly.

As shown in FIG. 5, in an image processing method based on contrast-enhanced ultrasound images according to an embodiment of the present application, the step of performing a second decoupling operation on the second contrast-enhanced ultrasound image sequence to generate a third contrast-enhanced ultrasound image sequence corresponding to the second contrast-enhanced ultrasound image sequence includes the following steps.

Step 21, determining a one-dimensional grayscale fluctuation signal corresponding to each of a plurality of pixel coordinates based on the plurality of pixel coordinates corresponding to the second contrast-enhanced ultrasound image sequence and a pixel value set corresponding to each of the plurality of pixel coordinates.

Based on an acquisition method of the contrast-enhanced ultrasound image sequence, it can be clearly known that the second contrast-enhanced ultrasound image sequence includes a plurality of second contrast-enhanced ultrasound images, and image sequence information based on time is included between the plurality of second contrast-enhanced ultrasound images. Image sizes of the plurality of second contrast-enhanced ultrasound images are the same. Then, correspondingly, after a space coordinate system (such as an XYZ three-dimensional space coordinate system, in which X axis and Y axis represent the pixel coordinates, and Z axis represents the image acquisition sequence or order in time dimension) is established based on the plurality of second contrast-enhanced ultrasound images, each pixel coordinate in an XY plane corresponds to a pixel value set. The pixel value set is a set of pixel values of the plurality of second contrast-enhanced ultrasound images at the pixel coordinate.

After the splicing operation based on the time dimension is performed on the pixel value set corresponding to each pixel coordinate based on the image sequence information included in the second contrast-enhanced ultrasound image sequence, the one-dimensional grayscale fluctuation signal corresponding to the pixel coordinate may be formed.

Step 22, generating the third contrast-enhanced ultrasound image sequence corresponding to the second contrast-enhanced ultrasound image sequence based on the one-dimensional grayscale fluctuation signal corresponding to each of the plurality of pixel coordinates.

Exemplarily, for each pixel coordinate in the plurality of pixel coordinates mentioned in Step 22, a multi-scale decomposition operation (such as Haar wavelet decomposition, Daubechies wavelet decomposition, etc.) is performed on the one-dimensional grayscale fluctuation signal corresponding to the pixel coordinate, and the third contrast-enhanced ultrasound image sequence corresponding to the second contrast-enhanced ultrasound image sequence is generated based on the obtained multi-scale decomposition signal.

By determining the one-dimensional grayscale fluctuation signal corresponding to each of the plurality of pixel coordinates based on the plurality of pixel coordinates corresponding to the second contrast-enhanced ultrasound image sequence and the pixel value set corresponding to each of the plurality of pixel coordinates and generating the third contrast-enhanced ultrasound image sequence corresponding to the second contrast-enhanced ultrasound image sequence based on the one-dimensional grayscale fluctuation signal corresponding to each of the plurality of pixel coordinates, the image processing method based on contrast-enhanced ultrasound images according to the embodiment of the present application achieves a purpose of performing the second decoupling operation on the second contrast-enhanced ultrasound image sequence to generate the third contrast-enhanced ultrasound image sequence corresponding to the second contrast-enhanced ultrasound image sequence. By calculating the one-dimensional grayscale fluctuation signal corresponding to the pixel coordinate, and performing the multi-scale decomposition operation on the one-dimensional grayscale fluctuation signal, the embodiment of the present application achieves a purpose of improving the temporal sparsity of the microbubbles, and effectively suppresses the noise in the background region of the second contrast-enhanced ultrasound image sequence, thereby further providing the prerequisite for improving accuracy of microbubble localization.

Figure 6:
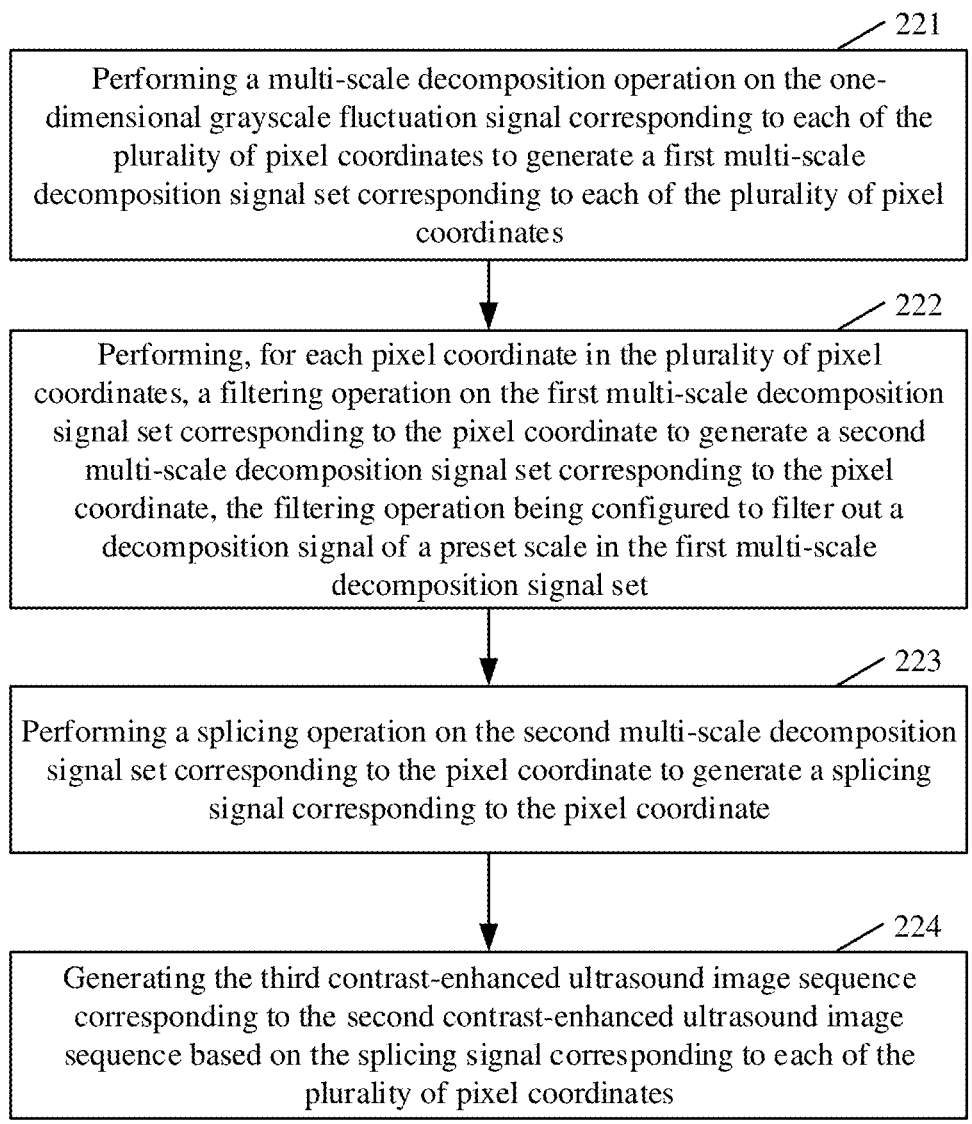
FIG. 6 is a schematic flowchart of generating the third contrast-enhanced ultrasound image sequence corresponding to the second contrast-enhanced ultrasound image sequence based on the one-dimensional grayscale fluctuation signal corresponding to each of the plurality of pixel coordinates according to an exemplary embodiment of the present application.

FIG. 6 is a schematic flowchart of generating the third contrast-enhanced ultrasound image sequence corresponding to the second contrast-enhanced ultrasound image sequence based on the one-dimensional grayscale fluctuation signal corresponding to each of the plurality of pixel coordinates according to an exemplary embodiment of the present application. The embodiment of the present application shown in FIG. 6 is extended based on the embodiment of the present application shown in FIG. 5. Differences between the embodiment shown in FIG. 6 and the embodiment shown in FIG. 5 are emphatically described below, and similarities may not be described repeatedly.

As shown in FIG. 6, in the image processing method based on contrast-enhanced ultrasound images according to an embodiment of the present application, the step of generating the third contrast-enhanced ultrasound image sequence corresponding to the second contrast-enhanced ultrasound image sequence based on the one-dimensional grayscale fluctuation signal corresponding to each of the plurality of pixel coordinates includes the following steps.

Step 221, performing a multi-scale decomposition operation on the one-dimensional grayscale fluctuation signal corresponding to each of the plurality of pixel coordinates to generate a first multi-scale decomposition signal set corresponding to each of the plurality of pixel coordinates.

Exemplarily, the multi-scale decomposition operation with a decomposition scale of 5 is performed on the one-dimensional grayscale fluctuation signal corresponding to each pixel coordinate based on Haar wavelet to generate the first multi-scale decomposition signal set corresponding to the pixel coordinate.

Step 222, performing, for each pixel coordinate in the plurality of pixel coordinates, a filtering operation on the first multi-scale decomposition signal set corresponding to the pixel coordinate to generate a second multi-scale decomposition signal set corresponding to the pixel coordinate, the filtering operation being used to filter out a decomposition signal of a preset scale in the first multi-scale decomposition signal set.

In an embodiment of the present application, the decomposition signal of the preset scale includes a decomposition signal with a smallest scale in the first multi-scale decomposition signal set. For example, a total of 5 decomposition scales are included, which are 1, 2, 3, 4 and 5, respectively. Then, the decomposition signal corresponding to decomposition scale 1 is filtered out, and the decomposition signals of decomposition scales 2 to 5 are retained. Based on a principle of multi-scale decomposition of signals, the inventor of the present application found that the smaller the decomposition scale, the more noise signals contained in the decomposition signal corresponding to the decomposition scale. Therefore, the embodiment of the present application achieves a purpose of efficiently filtering out the noise signal by filtering out the decomposition signal with the smallest scale.

A number of decomposition signals filtered out by the filtering operation is not limited to one as mentioned in the above embodiment and may also be multiple. For example, two decomposition signals with the smallest and a second smallest scales are filtered out.

Step 223, performing a splicing operation on the second multi-scale decomposition signal set corresponding to the pixel coordinate to generate a splicing signal corresponding to the pixel coordinate.

Exemplarily, for the second multi-scale decomposition signal set corresponding to each of the pixel coordinates, the splicing operation is performed on the decomposition signals corresponding to decomposition scales sequentially in an ascending order of decomposition levels or scales to generate a splicing signal corresponding to the pixel coordinate.

Step 224, generating the third contrast-enhanced ultrasound image sequence corresponding to the second contrast-enhanced ultrasound image sequence based on the splicing signal corresponding to each of the plurality of pixel coordinates.

Exemplarily, the splicing signals corresponding to each of the plurality of pixel coordinates mentioned in Step 224 are combined together to generate the third contrast-enhanced ultrasound image sequence corresponding to the second contrast-enhanced ultrasound image sequence. For example, the second contrast-enhanced ultrasound image sequence is denoted as $S_G=\{S_G{}^j|j=1, 2, \ldots N\}$, and the third contrast-enhanced ultrasound image sequence is denoted as $S_s=\{S_s{}^j|j=1, 2, \ldots M\}$.

By performing a multi-scale decomposition operation on the one-dimensional grayscale fluctuation signal corresponding to each of the plurality of pixel coordinates to generate a first multi-scale decomposition signal set corresponding to each of the plurality of pixel coordinates, then performing, for each pixel coordinate in the plurality of pixel coordinates, a filtering operation on the first multi-scale decomposition signal set corresponding to the pixel coordinate to generate a second multi-scale decomposition signal set corresponding to the pixel coordinate, then performing a splicing operation on the second multi-scale decomposition signal set corresponding to the pixel coordinate to generate a splicing signal corresponding to the pixel coordinate, and at last generating the third contrast-enhanced ultrasound image sequence corresponding to the second contrast-enhanced ultrasound image sequence based on the splicing signal corresponding to each of the plurality of pixel coordinates, the image processing method based on contrast-enhanced ultrasound images according to the embodiment of the present application achieves a purpose of generating the third contrast-enhanced ultrasound image sequence corresponding to the second contrast-enhanced ultrasound image sequence based on the one-dimensional grayscale fluctuation signal corresponding to each of the plurality of pixel coordinates. The embodiment of the present application may further filter out noise signals in the image, break a limitation of low microbubble concentration in traditional ultrasound localization microscopy, greatly improve the accuracy and speed of microbubble localization, and further greatly improve the accuracy and speed of subsequent super-resolution reconstruction.

A specific implementation process of the image processing method based on the contrast-enhanced ultrasound images mentioned in the embodiment shown in FIG. 6 will be described below with reference to FIG. 7.

Figure 7:
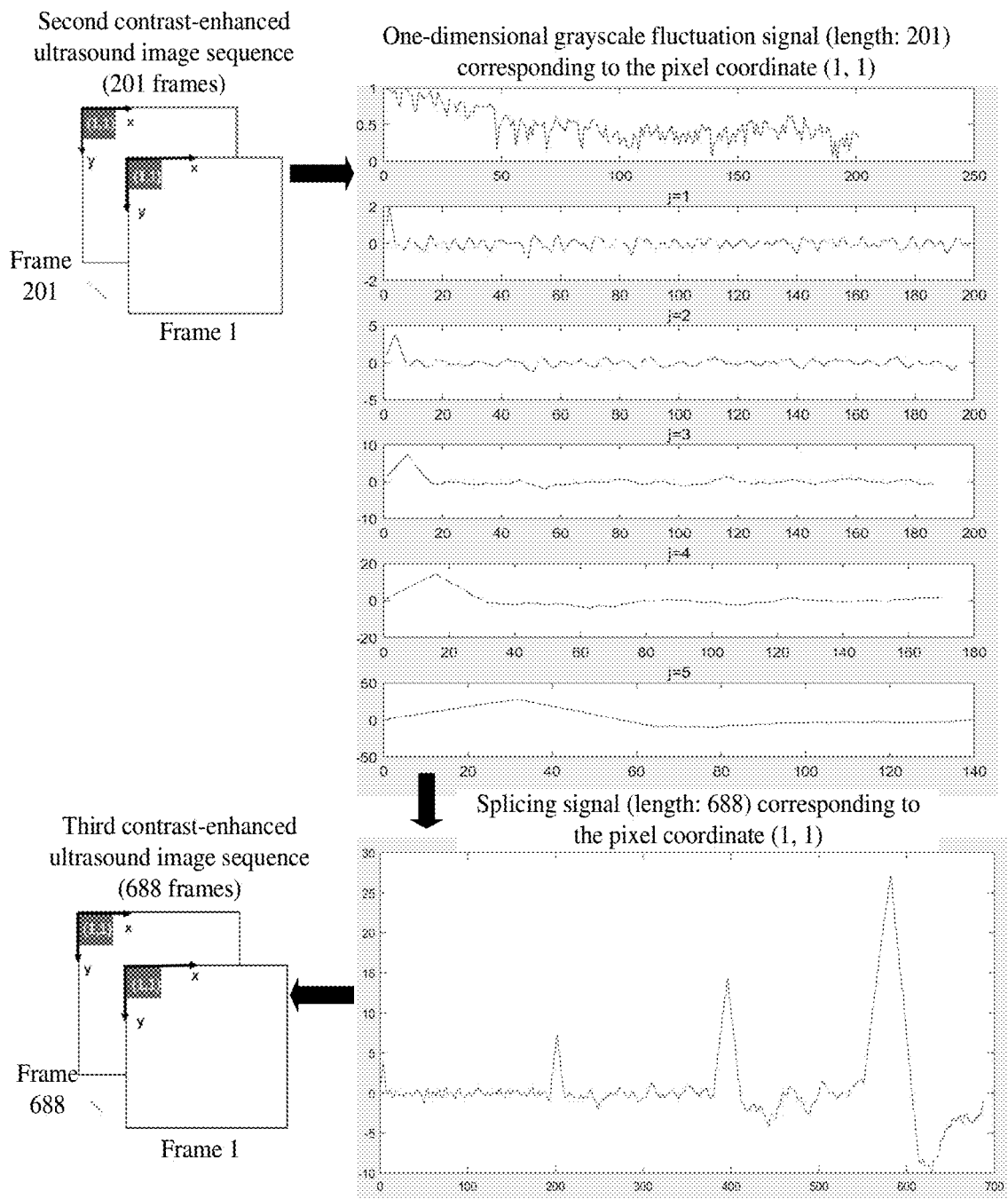
FIG. 7 is a schematic diagram showing a staged result of generating the third contrast-enhanced ultrasound image sequence corresponding to the second contrast-enhanced ultrasound image sequence based on the one-dimensional grayscale fluctuation signal corresponding to each of the plurality of pixel coordinates according to an exemplary embodiment of the present application.

FIG. 7 is a schematic diagram showing a staged result of generating the third contrast-enhanced ultrasound image sequence corresponding to the second contrast-enhanced ultrasound image sequence based on the one-dimensional grayscale fluctuation signal corresponding to each of the plurality of pixel coordinates according to an exemplary embodiment of the present application.

As shown in FIG. 7, the second contrast-enhanced ultrasound image sequence generated after the first decoupling operation has 201 frames in total, and the following description takes the pixel coordinate (1, 1) as an example.

First step, extracting the grayscale values (201 in total) at the pixel coordinate (1, 1) in frames 1 to 201, and forming the one-dimensional grayscale fluctuation signal with a length of 201 according to the image acquisition sequence or order.

Second step, performing the multi-scale decomposition operation on a one-dimensional grayscale fluctuation signal formed above. Specifically, Haar wavelet is used for the multi-scale decomposition operation, and a number of decomposition scale is 5. The decomposition signals corresponding to different decomposition scales are calculated respectively based on the decomposition scale j and the one-dimensional grayscale fluctuation signal. The multi-scale decomposition operation based on Haar wavelet mainly uses a convolution calculation method to determine the decomposition signal corresponding to each decomposition scale, which is not repeated in this embodiment of the present application.

After calculation, it is known that a length of the decomposition signal corresponding to the decomposition scale j=1 is 198, a length of the decomposition signal corresponding to the decomposition scale j=2 is 194, a length of the decomposition signal corresponding to the decomposition scale j=3 is 186, a length of the decomposition signal corresponding to the decomposition scale j=4 is 170, and a length of the decomposition signal corresponding to the decomposition scale j=5 is 138.

As mentioned above, relatively speaking, the decomposition signal corresponding to a smaller decomposition scale includes more noise signals. Therefore, in the embodiment of the present application, the decomposition signal corresponding to the decomposition scale j=1 is filtered out, and the decomposition signals corresponding to the decomposition scale j=2 to 5 are retained.

Third step, splicing the decomposition signals corresponding to the decomposition scales j=2~5 to generate a splicing signal with a length of 688 based on an ascending order of the decomposition levels or scales. The splicing signal determined above may characterize a grayscale fluctuation situation at the pixel coordinate (1, 1).

Fourth step, performing the operations of the first step to the third step for each pixel coordinate, thereby obtaining the splicing signal corresponding to each pixel coordinate. The length of the splicing signal corresponding to each pixel coordinate is 688. Finally, a third contrast-enhanced ultrasound image sequence including 688 images is generated based on the splicing signal corresponding to each pixel coordinate.

It can be seen that the embodiments of the present application achieve the temporal sparsity of the microbubbles. The temporal sparsity together with the spatial sparsity mentioned above forms the spatial-temporal sparsity of the microbubbles. The microbubbles with spatial-temporal sparsity are helpful to improve the accuracy of microbubble localization.

Figure 8:
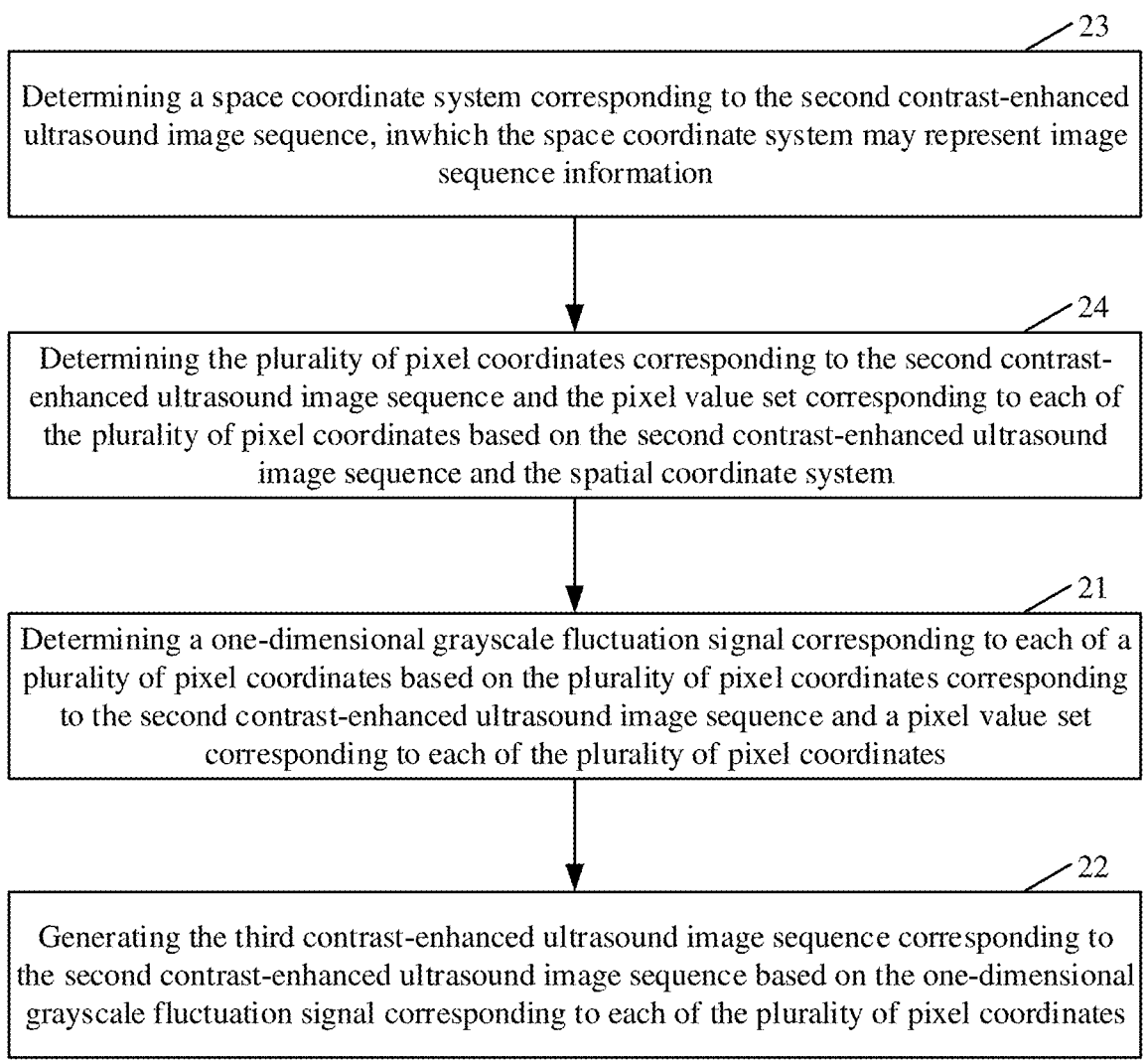
FIG. 8 is a schematic flowchart of performing a second decoupling operation on the second contrast-enhanced ultrasound image sequence to generate a third contrast-enhanced ultrasound image sequence corresponding to the second contrast-enhanced ultrasound image sequence according to another exemplary embodiment of the present application.

FIG. 8 is a schematic flowchart of performing a second decoupling operation on the second contrast-enhanced ultrasound image sequence to generate a third contrast-enhanced ultrasound image sequence corresponding to the second contrast-enhanced ultrasound image sequence according to another exemplary embodiment of the present application. The embodiment of the present application shown in FIG. 8 is extended based on the embodiment of the present application shown in FIG. 5. Differences between the embodiment shown in FIG. 8 and the embodiment shown in FIG. 5 are emphatically described below, and similarities may not be described repeatedly.

As shown in FIG. 8, in the image processing method based on contrast-enhanced ultrasound images according to an embodiment of the present application, before the step of determining a one-dimensional grayscale fluctuation signal corresponding to each of a plurality of pixel coordinates based on the plurality of pixel coordinates corresponding to the second contrast-enhanced ultrasound image sequence and a pixel value set corresponding to each of the plurality of pixel coordinates, the image processing method further includes the following steps.

Step 23, determining a space coordinate system corresponding to the second contrast-enhanced ultrasound image sequence, the space coordinate system being able to represent image sequence information.

Exemplarily, the space coordinate system is a three-dimensional space coordinate system including an X axis, a Y axis and a Z axis. The X axis and the Y axis are pixel coordinate axes, and the Z axis represents the image acquisition sequence or order.

Step 24, determining the plurality of pixel coordinates corresponding to the second contrast-enhanced ultrasound image sequence and the pixel value set corresponding to each of the plurality of pixel coordinates based on the second contrast-enhanced ultrasound image sequence and the spatial coordinate system.

The image processing method based on contrast-enhanced ultrasound images according to the embodiment of the present application improves an accuracy of the pixel value set corresponding to the pixel coordinates determined above by means of the space coordinate system, thereby providing the prerequisite for improving the accuracy of microbubble localization.

Figure 9:
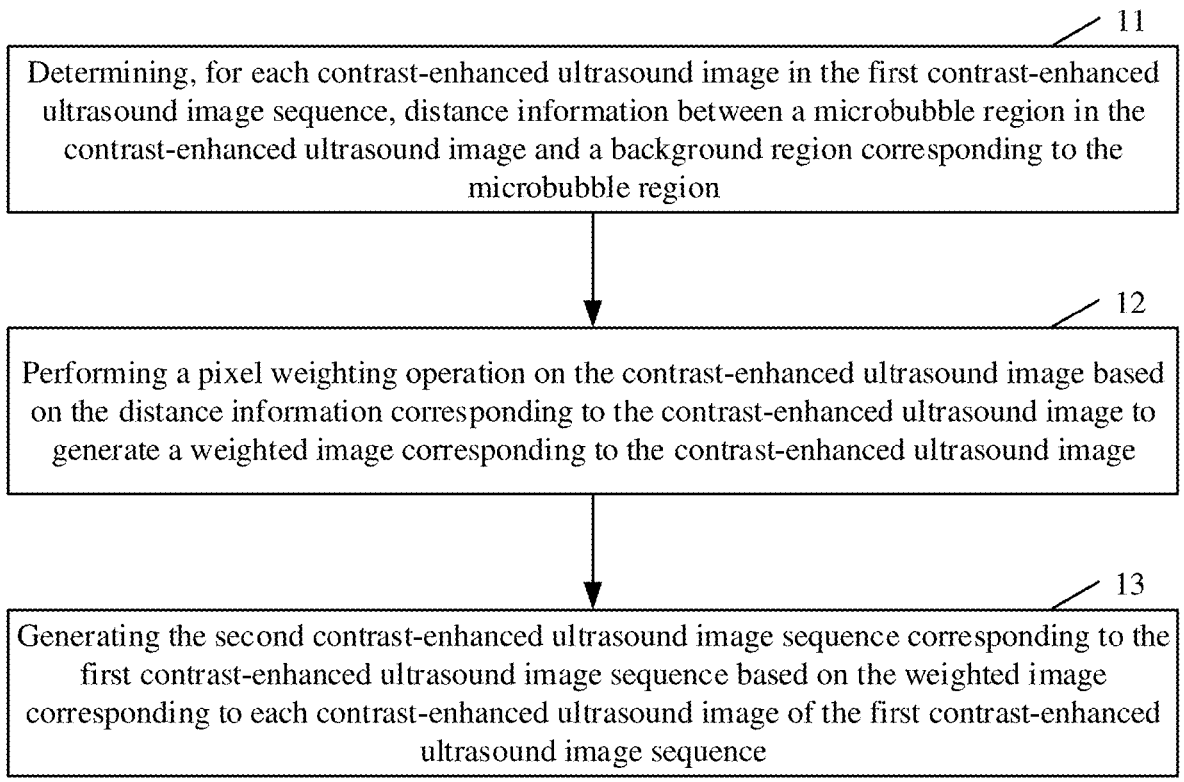
FIG. 9 is a schematic flowchart of performing a first decoupling operation on the first contrast-enhanced ultrasound image sequence to generate a second contrast-enhanced ultrasound image sequence corresponding to the first contrast-enhanced ultrasound image sequence according to an exemplary embodiment of the present application.

FIG. 9 is a schematic flowchart of performing a first decoupling operation on the first contrast-enhanced ultrasound image sequence to generate a second contrast-enhanced ultrasound image sequence corresponding to the first contrast-enhanced ultrasound image sequence according to an exemplary embodiment of the present application. The embodiment of the present application shown in FIG. 9 is extended based on the embodiment of the present application shown in FIG. 3. Differences between the embodiment shown in FIG. 9 and the embodiment shown in FIG. 3 are emphatically described below, and similarities may not be described repeatedly.

As shown in FIG. 9, in the image processing method based on contrast-enhanced ultrasound images according to an embodiment of the present application, the step of performing a first decoupling operation on the first contrast-enhanced ultrasound image sequence to generate a second contrast-enhanced ultrasound image sequence corresponding to the first contrast-enhanced ultrasound image sequence, includes the following steps.

Step 11, determining, for each contrast-enhanced ultrasound image in the first contrast-enhanced ultrasound image sequence, distance information between a microbubble region in the contrast-enhanced ultrasound image and a background region corresponding to the microbubble region.

Figure 10:
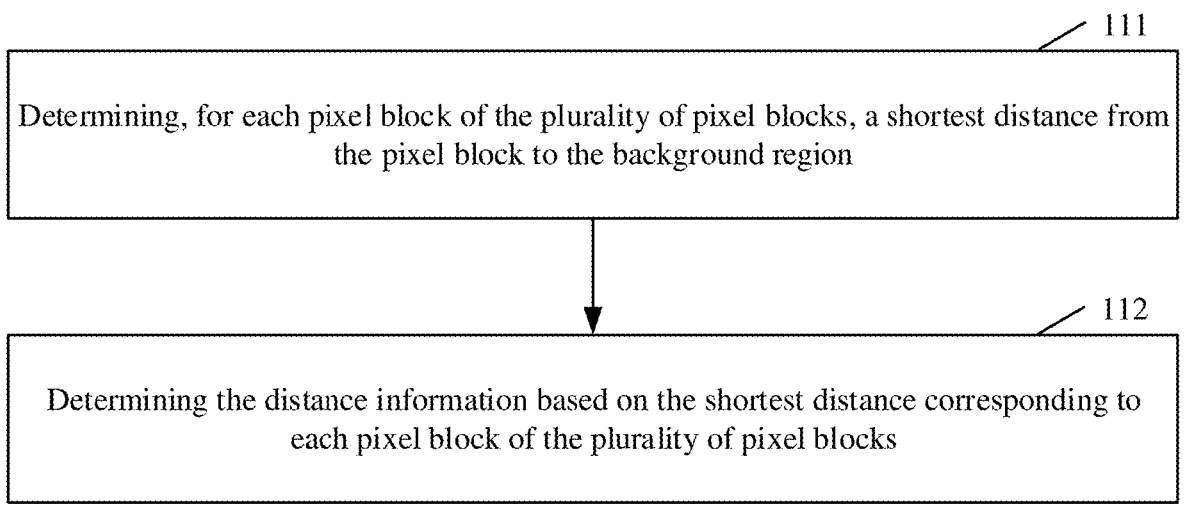
FIG. 10 is a schematic flowchart of determining distance information between a microbubble region in the contrast-enhanced ultrasound image and a background region corresponding to the microbubble region according to an exemplary embodiment of the present application.

FIG. 10 is a schematic flowchart of determining distance information between a microbubble region in the contrast-enhanced ultrasound image and a background region corresponding to the microbubble region according to an exemplary embodiment of the present application. As shown in FIG. 10, in embodiments of the present application, the microbubble region includes a plurality of pixel blocks, and determining distance information between a microbubble region in the contrast-enhanced ultrasound image and a background region corresponding to the microbubble region (Step 11), includes the following steps.

Step 111, determining, for each pixel block of the plurality of pixel blocks, a shortest distance from the pixel block to the background region.

Step 112, determining the distance information based on the shortest distance corresponding to each pixel block of the plurality of pixel blocks.

Exemplarily, the shortest distance mentioned in Step 111 is Euclidean distance or Manhattan distance.

For example, the pixel block mentioned above is a separate pixel unit, and correspondingly, the pixel coordinate corresponding to the pixel block is the pixel coordinate corresponding to the pixel unit. For another example, the above-mentioned pixel block is a pixel block formed by a plurality of adjacent pixel units, and correspondingly, the pixel coordinate corresponding to the pixel block is the pixel coordinate at a center point of the plurality of pixel units.

Step 12, performing a pixel weighting operation on the contrast-enhanced ultrasound image based on the distance information corresponding to the contrast-enhanced ultrasound image to generate a weighted image corresponding to the contrast-enhanced ultrasound image.

In an embodiment of the present application, a pixel grayscale value and a shortest distance corresponding to a pixel coordinate are determined respectively based on each pixel coordinate corresponding to the microbubble region, and then the shortest distance is multiplied by the pixel grayscale value to determine a weighted value corresponding to the pixel coordinate (that is a new pixel grayscale value), and then a weighted image corresponding to the contrast-enhanced ultrasound image is finally determined.

Compared with a marginal region of the microbubble region, a shortest distance value between a central region of the microbubble region and the background region is larger. Therefore, after the pixel weighting operation is performed on the contrast-enhanced ultrasound image based on the distance information, the microbubble region of the contrast-enhanced ultrasound image may be effectively highlighted (that is, enhanced), and the noise in the background region may be suppressed.

Step 13, generating the second contrast-enhanced ultrasound image sequence corresponding to the first contrast-enhanced ultrasound image sequence based on the weighted image corresponding to each contrast-enhanced ultrasound image of the first contrast-enhanced ultrasound image sequence.

The image processing method based on the contrast-enhanced ultrasound images according to the embodiment of the present application may effectively highlight (that is, enhance) the central (along microbubble trajectory) region of the microbubbles in the contrast-enhanced ultrasound image, and suppress the noise in the background region, thereby further realizing a preliminary decoupling of overlapping microbubbles, and providing the prerequisite for improving the accuracy of microbubble localization.

In an embodiment of the present application, determining distance information between a microbubble region in the contrast-enhanced ultrasound image and a background region corresponding to the microbubble region includes: performing a binarization processing on the contrast-enhanced ultrasound image based on the microbubble region and the background region to generate a binarized image; and determining the distance information between the microbubble region and the background region based on the binarized image.

After the binarization processing is performed on the contrast-enhanced ultrasound image according to the embodiment of the present application, the calculation procedure of the step of generating the weighted image corresponding to the contrast-enhanced ultrasound image may be simplified, thereby improving a speed of image processing.

Figure 11:
FIG. 11 is a schematic diagram showing a process of generating a weighted image according to an exemplary embodiment of the present application.
Figure 12A:
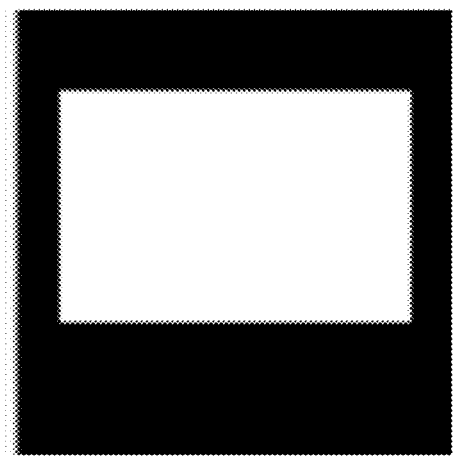
FIG. 12a and FIG. 12b are schematic diagrams showing a weighting effect of a pixel weighting operation according to an exemplary embodiment of the present application.
Figure 12B:
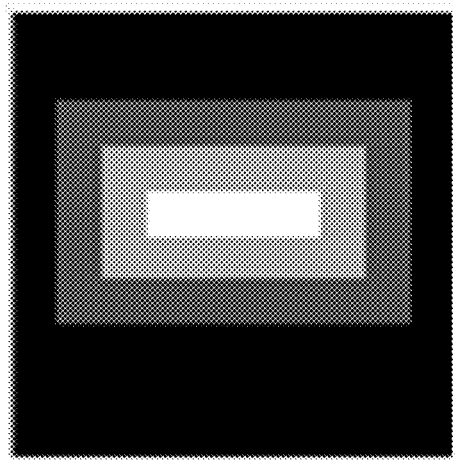

The following describes an application effect of the first decoupling operation mentioned in the embodiments shown in FIG. 9 and FIG. 10 with reference to FIG. 11, FIG. 12a and FIG. 12b. It should be noted that, in order to clearly present the application effect of the first decoupling operation, FIG. 11, FIG. 12a and FIG. 12b show a two-dimensional image including a rectangle (analogous to microbubbles) as an example.

FIG. 11 is a schematic diagram showing a process of generating a weighted image according to an exemplary embodiment of the present application. Specifically, the image on the left side of FIG. 11 is a pixel distribution diagram of a two-dimensional image. A pixel value of the pixel coordinate corresponding to the rectangular region (analogous to the microbubble region) is set to 1, and the pixel value of the pixel coordinate corresponding to the background region is set to 0. The image on the right side of FIG. 11 is a pixel distribution diagram of a weighted image obtained by performing a distance weighting on the image on the left side of FIG. 11. The shortest distance here is determined by "chessboard distance", and the shortest distance corresponding to each pixel coordinate is multiplied by an original pixel value to obtain the image on the right side of FIG. 11.

FIG. 12a and FIG. 12b are schematic diagrams showing a weighting effect of a pixel weighting operation according to an exemplary embodiment of the present application. Specifically, FIG. 12a shows an imaging effect corresponding to the image on the left side of FIG. 11, and FIG. 12b shows an imaging effect corresponding to the image on the right side of FIG. 11. Based on what is shown in FIG. 12a and FIG. 12b, it can be clearly known that after the first decoupling operation is performed, the central region of the rectangle in the two-dimensional image is enhanced (that is, highlighted), and the marginal region is weakened. It can be seen that, after the first decoupling operation is performed, the central region of the microbubble region in the contrast-enhanced ultrasound image may be enhanced (that is, may be highlighted), and the marginal region may be weakened.

Figure 13:
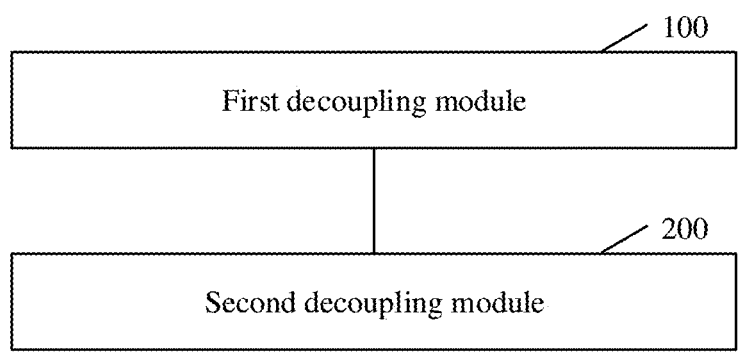
FIG. 13 is a schematic structural diagram of an image processing apparatus based on contrast-enhanced ultrasound images according to an exemplary embodiment of the present application.

FIG. 13 is a schematic structural diagram of an image processing apparatus based on contrast-enhanced ultrasound images according to an exemplary embodiment of the present application. As shown in FIG. 13, an image processing apparatus based on contrast-enhanced ultrasound images according to embodiments of the present application is applied to a first contrast-enhanced ultrasound image sequence including microbubbles and includes the following modules.

A first decoupling module 100, configured to perform a first decoupling operation on the first contrast-enhanced ultrasound image sequence to generate a second contrast-enhanced ultrasound image sequence corresponding to the first contrast-enhanced ultrasound image sequence. The first decoupling operation is used to improve spatial sparsity of the microbubbles.

A second decoupling module 200, configured to perform a second decoupling operation on the second contrast-enhanced ultrasound image sequence to generate a third contrast-enhanced ultrasound image sequence corresponding to the second contrast-enhanced ultrasound image sequence. The second decoupling operation is used to improve temporal sparsity of the microbubbles.

In an embodiment of the present application, the first decoupling module 100 is further configured to: determine, for each contrast-enhanced ultrasound image in the first contrast-enhanced ultrasound image sequence, distance information between a microbubble region in the contrast-enhanced ultrasound image and a background region corresponding to the microbubble region; and perform a pixel weighting operation on the contrast-enhanced ultrasound image based on the distance information corresponding to the contrast-enhanced ultrasound image to generate a weighted image corresponding to the contrast-enhanced ultrasound image; and then generate the second contrast-enhanced ultrasound image sequence corresponding to the first contrast-enhanced ultrasound image sequence based on the weighted image corresponding to each contrast-enhanced ultrasound image of the first contrast-enhanced ultrasound image sequence.

Figure 14:
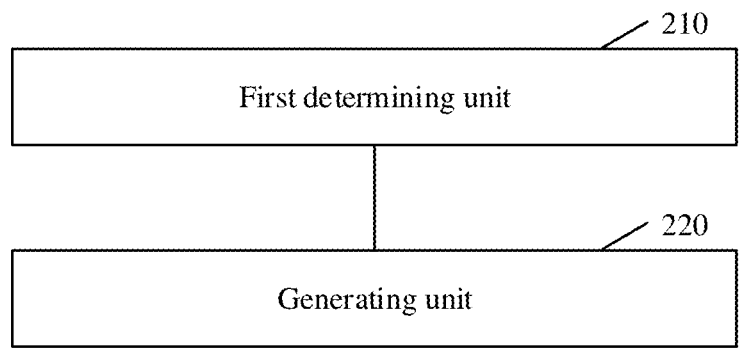
FIG. 14 is a schematic structural diagram of a second decoupling module according to an exemplary embodiment of the present application.

FIG. 14 is a schematic structural diagram of a second decoupling module according to an exemplary embodiment of the present application. The embodiment of the present application shown in FIG. 14 is extended based on the embodiment of the present application shown in FIG. 13. Differences between the embodiment shown in FIG. 14 and the embodiment shown in FIG. 13 are emphatically described below, and similarities may not be described repeatedly.

As shown in FIG. 14, in the image processing apparatus based on contrast-enhanced ultrasound images according to embodiments of the present application, the second decoupling module 200 includes the following units.

A first determining unit 210, configured to determine a one-dimensional grayscale fluctuation signal corresponding to each of a plurality of pixel coordinates based on the plurality of pixel coordinates corresponding to the second contrast-enhanced ultrasound image sequence and a pixel value set corresponding to each of the plurality of pixel coordinates.

A generating unit 220, configured to generate a third contrast-enhanced ultrasound image sequence corresponding to the second contrast-enhanced ultrasound image sequence based on the one-dimensional grayscale fluctuation signal corresponding to each of the plurality of pixel coordinates.

In an embodiment of the present application, the generating unit 220 is further configured to: perform a multi-scale decomposition operation on the one-dimensional grayscale fluctuation signal corresponding to each of the plurality of pixel coordinates to generate a first multi-scale decomposition signal set corresponding to each of the plurality of pixel coordinates; and perform, for each pixel coordinate in the plurality of pixel coordinates, a filtering operation on the first multi-scale decomposition signal set corresponding to the pixel coordinate to generate a second multi-scale decomposition signal set corresponding to the pixel coordinate; and then perform a splicing operation on the second multi-scale decomposition signal set corresponding to the pixel coordinate to generate a splicing signal corresponding to the pixel coordinate; and generate the third contrast-enhanced ultrasound image sequence corresponding to the second contrast-enhanced ultrasound image sequence based on the splicing signal corresponding to each of the plurality of pixel coordinates.

Figure 15:
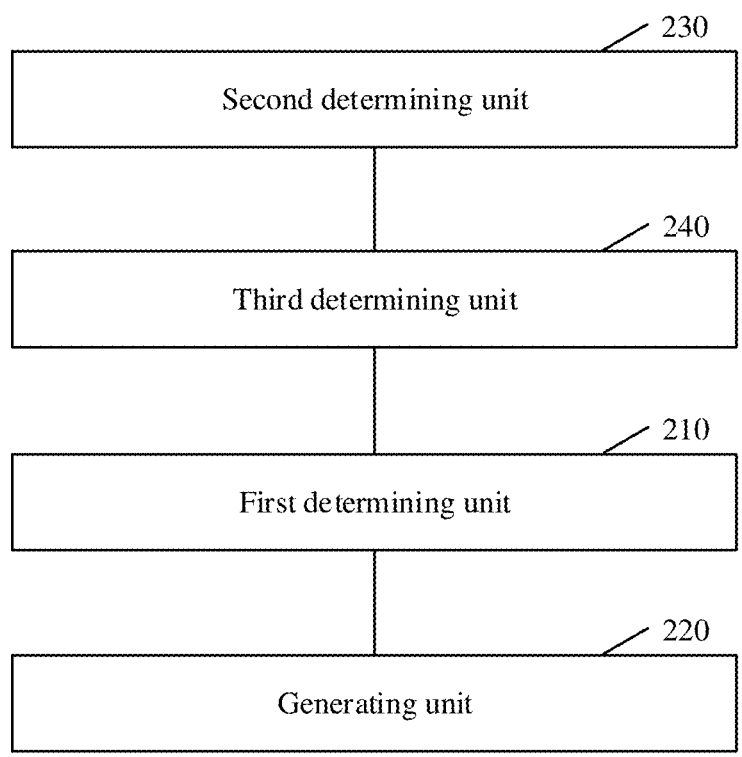
FIG. 15 is a schematic structural diagram of a second decoupling module according to another exemplary embodiment of the present application.

FIG. 15 is a schematic structural diagram of a second decoupling module according to another exemplary embodiment of the present application. The embodiment of the present application shown in FIG. 15 is extended based on the embodiment of the present application shown in FIG. 14. Differences between the embodiment shown in FIG. 15 and the embodiment shown in FIG. 14 are emphatically described below, and similarities may not be described repeatedly.

As shown in FIG. 15, in the image processing apparatus based on contrast-enhanced ultrasound images according to embodiments of the present application, the second decoupling module 200 further includes the following units.

A second determining unit 230, configured to determine a space coordinate system corresponding to the second contrast-enhanced ultrasound image sequence. The space coordinate system may represent image sequence information.

A third determining unit 240, configured to determine the plurality of pixel coordinates corresponding to the second contrast-enhanced ultrasound image sequence and the pixel value set corresponding to each of the plurality of pixel coordinates based on the second contrast-enhanced ultrasound image sequence and the spatial coordinate system.

Operations and functions of the first decoupling module 100, the second decoupling module 200, and the first determining unit 210, the generating unit 220, the second determining unit 230, and third determining unit 240 included in the second decoupling module 200 in the image processing apparatus based on contrast-enhanced ultrasound images provided in FIG. 13 to FIG. 15, may refer to the image processing method based on contrast-enhanced ultrasound images provided in FIG. 3 to FIG. 10. In order to avoid repetitions, details are not repeated here.

Figure 16:
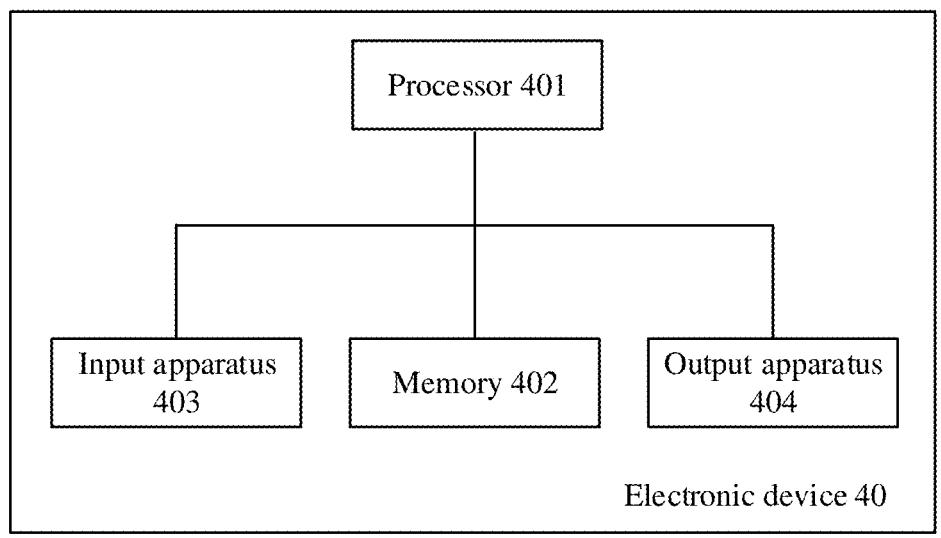
FIG. 16 is a schematic structural diagram of an electronic device according to an exemplary embodiment of the present application.

Hereinafter, an electronic device according to embodiments of the present application will be described with reference to FIG. 16. FIG. 16 is a schematic structural diagram of an electronic device according to an exemplary embodiment of the present application.

As shown in FIG. 16, the electronic device 40 includes one or more processors 401 and a memory 402.

The processor 401 may be a Central Processing Unit (CPU) or another form of processing unit with data processing capability and/or instruction execution capability and may control another component in the electronic device to perform an expected function.

The memory 402 may include one or more computer program products, which may include various forms of computer-readable storage media, such as a volatile memory and/or non-volatile memory. The volatile memory may include, for example, a Random Access Memory (RAM) and/or a cache (cache). The non-volatile memory may include, for example, a Read-Only Memory (ROM), a hard disk, and a flash memory. The compute-readable storage medium may store one or more computer program instructions, and the processor 401 may run the image processing method based on contrast-enhanced ultrasound images and/or other expected functions of the embodiments in the present application described above. The compute-readable storage medium may further store information, such as a weighted image, or the like.

In an example, the electronic device 40 may further include an input apparatus 403 and an output apparatus 404, and these components are interconnected via a bus system and/or another form of connection mechanism (not shown).

The input apparatus 403 may also include, for example, a keyboard, a mouse, and so on.

The output apparatus 404 may output various information such as the third contrast-enhanced ultrasound image sequence determined above to the outside. The output device 404 may include, for example, a display, a communication network and a remote output device connected to it, and so on.

Certainly, for simplicity, only some of the components related to the present application in the electronic device 40 are shown in FIG. 16, and components such as a bus, and an input/output interface are omitted. In addition, the electronic device 40 may further include any other suitable component depending on a specific application case.

In addition to the foregoing methods and devices, an embodiment of the present application may also be a computer program product that includes computer program instructions. When the computer program instructions are run by a processor, the processor is enabled to perform the steps of the image processing method based on contrast-enhanced ultrasound images according to the embodiments of the present application described in the "Exemplary Methods" part of this specification.

The computer program product may write program code for performing the operations of the embodiments of the present application in any combination of one or more programming languages, and the programming languages include object-oriented programming languages such as Java and C++, and further include conventional procedural programming languages such as "C" or similar programming languages. The program code may be executed entirely on a user computing device, partly on a user device, as a stand-alone software package, partly on a user computing device while partly on a remote computing device, or entirely on a remote computing device or a server.

In addition, an embodiment of the present application may also be a computer-readable storage medium, where the computer-readable storage medium stores computer program instructions. When the computer program instructions are run by a processor, the processor is enabled to perform the steps of the image processing method based on contrast-enhanced ultrasound images according to the embodiments of the present application described in the "Exemplary Methods" part of this specification.

The computer-readable storage medium may use any combination of one or more readable media. The readable medium may be a readable signal medium or a readable storage medium. The readable storage medium may include, for example, but not limited to, an electronic, magnetic, optical, electromagnetic, infrared, or semiconductor system, apparatus, or means, or any combination of the above. More specific examples (a non-exhaustive list) of the readable storage medium include: an electrical connection having one or more wires, a portable computer disk, a hard disk, a Random Access Memory (RAM), a Read-Only Memory (ROM), an Erasable Programmable Read-Only Memory (EPROM or a flash memory), an optical fiber, a portable Compact Disk Read-Only Memory (CD-ROM), an optical storage means, a magnetic storage means, or any suitable combination of the above.

The foregoing describes basic principles of the present application with reference to specific embodiments. However, it may be noted that the merits, advantages, effects, and the like mentioned in the present application are merely examples but not limitations, and cannot be considered that these merits, advantages, effects, and the like are essential to the embodiments of the present application. In addition, the specific details disclosed above are intended only for the purpose of illustration and convenience of understanding, and are not limited thereto, and are not intended to limit the present application to the specific details described above.

The block diagrams of components, apparatuses, devices and systems in the present application are merely illustrative examples and are not intended to require or imply that connections, arrangements and configurations must be performed in the manner shown in the block diagrams. As will be recognized by those skilled in the art, these components, apparatuses, devices and systems can be connected, arranged and configured in any manner. Terms such as "comprise", "include", "have" are open words, meaning "include but not limited to", and they can be used interchangeably. Terms "or" and "and" used herein refer to "and/or", and they can be used interchangeably unless the context expressly indicates otherwise. Term "such as" used herein refers to "such as but not limited to" and they can be used interchangeably.

It may also be noted that, in the apparatuses, devices and methods of the present application, components or steps can be decomposed and/or recombined. These decompositions and/or recombination shall be considered as equivalent solutions of the present application.

The foregoing descriptions of the disclosed aspects are provided to enable any person skilled in the art to make or use the present application. Modifications to these aspects are very obvious to those skilled in the art and the general principles defined herein can be applied to other aspects without departing from the scope of the present application. Therefore, the present application is not intended to be limited to the aspects shown herein, but to the widest extent consistent with the principles and novel features disclosed herein.

The above description has been presented for the purposes of illustration and description. Furthermore, this description is not intended to limit the embodiments of the present application to the forms disclosed herein. Although a number of example aspects and embodiments have been discussed above, those skilled in the art will recognize certain variations, modifications, changes, additions and sub-combinations thereof.

What is claimed is:

1. An image processing method based on contrast-enhanced ultrasound images, applied to a first contrast-enhanced ultrasound image sequence comprising microbubbles, comprising:
    performing a first decoupling operation on the first contrast-enhanced ultrasound image sequence to generate a second contrast-enhanced ultrasound image sequence corresponding to the first contrast-enhanced ultrasound image sequence, the first decoupling operation being used to improve spatial sparsity of the microbubbles; and
    performing a second decoupling operation on the second contrast-enhanced ultrasound image sequence to generate a third contrast-enhanced ultrasound image sequence corresponding to the second contrast-enhanced ultrasound image sequence, the second decoupling operation being used to improve temporal sparsity of the microbubbles;
    wherein the performing a second decoupling operation on the second contrast-enhanced ultrasound image sequence to generate a third contrast-enhanced ultrasound image sequence corresponding to the second contrast-enhanced ultrasound image sequence comprises: determining one-dimensional grayscale fluctuation signals corresponding to a plurality of pixel coordinates respectively, based on the plurality of pixel coordinates corresponding to the second contrast-enhanced ultrasound image sequence and pixel value sets corresponding to the plurality of pixel coordinates respectively; and
    generating the third contrast-enhanced ultrasound image sequence corresponding to the second contrast-enhanced ultrasound image sequence based on the one-dimensional grayscale fluctuation signals corresponding to the plurality of pixel coordinates respectively;
    before the determining one-dimensional grayscale fluctuation signals corresponding to a plurality of pixel coordinates respectively, based on the plurality of pixel coordinates corresponding to the second contrast-enhanced ultrasound image sequence and pixel value sets corresponding to the plurality of pixel coordinates respectively, further comprising:
        determining a space coordinate system corresponding to the second contrast-enhanced ultrasound image sequence, the space coordinate system being capable to represent image sequence information; and
        determining the plurality of pixel coordinates corresponding to the second contrast-enhanced ultrasound image sequence and the pixel value sets corresponding to the plurality of pixel coordinates respectively, based on the second contrast-enhanced ultrasound image sequence and the spatial coordinate system.

2. The image processing method based on contrast-enhanced ultrasound images according to claim 1, wherein the generating the third contrast-enhanced ultrasound image sequence corresponding to the second contrast-enhanced ultrasound image sequence based on the one-dimensional grayscale fluctuation signals corresponding to the plurality of pixel coordinates respectively comprises:
    performing a multi-scale decomposition operation on the one-dimensional grayscale fluctuation signals corresponding to the plurality of pixel coordinates to generate first multi-scale decomposition signal sets corresponding to the plurality of pixel coordinates respectively;
    performing, for each pixel coordinate in the plurality of pixel coordinates, a filtering operation on the first multi-scale decomposition signal set corresponding to the pixel coordinate to generate a second multi-scale decomposition signal set corresponding to the pixel coordinate, the filtering operation being used to filter out a decomposition signal of a preset scale in the first multi-scale decomposition signal set;
    performing a splicing operation on the second multi-scale decomposition signal set corresponding to the pixel coordinate to generate a splicing signal corresponding to the pixel coordinate; and
    generating the third contrast-enhanced ultrasound image sequence corresponding to the second contrast-enhanced ultrasound image sequence based on splicing signals corresponding to the plurality of pixel coordinates respectively.

3. The image processing method based on contrast-enhanced ultrasound images according to claim 2, wherein the performing a splicing operation on the second multi-scale decomposition signal set corresponding to the pixel coordinate to generate a splicing signal corresponding to the pixel coordinate comprises:
    performing, for the second multi-scale decomposition signal set corresponding to the pixel coordinate, the splicing operation on decomposition signals corresponding to decomposition scales sequentially in an ascending order of decomposition levels or scales to generate the splicing signal corresponding to the pixel coordinate.

4. The image processing method based on contrast-enhanced ultrasound images according to claim 2, wherein the decomposition signal of the preset scale comprises a decomposition signal with a smallest scale in the first multi-scale decomposition signal set.

5. The image processing method based on contrast-enhanced ultrasound images according to claim 3, wherein the decomposition signal of the preset scale comprises a decomposition signal with a smallest scale in the first multi-scale decomposition signal set.

6. The image processing method based on contrast-enhanced ultrasound images according to claim 4, wherein the decomposition signal of the preset scale further comprises a decomposition signal with a second smallest scale in the first multi-scale decomposition signal set.

7. The image processing method based on contrast-enhanced ultrasound images according to claim 2, before the determining one-dimensional grayscale fluctuation signals corresponding to a plurality of pixel coordinates respectively, based on the plurality of pixel coordinates corresponding to the second contrast-enhanced ultrasound image sequence and pixel value sets corresponding to the plurality of pixel coordinates respectively, further comprising:
  determining a space coordinate system corresponding to the second contrast-enhanced ultrasound image sequence, the space coordinate system being capable to represent image sequence information; and
  determining the plurality of pixel coordinates corresponding to the second contrast-enhanced ultrasound image sequence and the pixel value sets corresponding to the plurality of pixel coordinates respectively, based on the second contrast-enhanced ultrasound image sequence and the spatial coordinate system.

8. The image processing method based on contrast-enhanced ultrasound images according to claim 1, wherein the determining one-dimensional grayscale fluctuation signals corresponding to a plurality of pixel coordinates respectively, based on the plurality of pixel coordinates corresponding to the second contrast-enhanced ultrasound image sequence and pixel value sets corresponding to the plurality of pixel coordinates respectively comprises:
  splicing, for each pixel coordinate in the plurality of pixel coordinates, the pixel value set corresponding to the pixel coordinate into the one-dimensional grayscale fluctuation signal based on image sequence order represented by a spatial coordinate system, so as to determine the one-dimensional grayscale fluctuation signals corresponding to the plurality of pixel coordinates respectively.

9. The image processing method based on contrast-enhanced ultrasound images according to claim 1, wherein the performing a first decoupling operation on the first contrast-enhanced ultrasound image sequence to generate a second contrast-enhanced ultrasound image sequence corresponding to the first contrast-enhanced ultrasound image sequence comprises:
  determining, for each contrast-enhanced ultrasound image in the first contrast-enhanced ultrasound image sequence, distance information between a microbubble region in the contrast-enhanced ultrasound image and a background region corresponding to the microbubble region;
  performing a pixel weighting operation on the contrast-enhanced ultrasound image based on the distance information corresponding to the contrast-enhanced ultrasound image to generate a weighted image corresponding to the contrast-enhanced ultrasound image; and
  generating the second contrast-enhanced ultrasound image sequence corresponding to the first contrast-enhanced ultrasound image sequence based on weighted images respectively corresponding to contrast-enhanced ultrasound images of the first contrast-enhanced ultrasound image sequence.

10. The image processing method based on contrast-enhanced ultrasound images according to claim 9, wherein the performing a pixel weighting operation on the contrast-enhanced ultrasound image based on the distance information corresponding to the contrast-enhanced ultrasound image to generate a weighted image corresponding to the contrast-enhanced ultrasound image comprises:
  determining, based on each pixel coordinate corresponding to the microbubble region, a pixel grayscale value and a shortest distance corresponding to the pixel coordinate;
  multiplying the pixel grayscale value and the shortest distance corresponding to the pixel coordinate to determine a weighted value corresponding to the pixel coordinate; and
  determining the weighted image corresponding to the contrast-enhanced ultrasound image based on weighted values respectively corresponding to all pixel coordinates corresponding to the microbubble region.

11. The image processing method based on contrast-enhanced ultrasound images according to claim 9, wherein the determining distance information between a microbubble region in the contrast-enhanced ultrasound image and a background region corresponding to the microbubble region comprises:
  performing a binarization processing on the contrast-enhanced ultrasound image based on the microbubble region and the background region to generate a binarized image; and
  determining the distance information between the microbubble region and the background region based on the binarized image.

12. The image processing method based on contrast-enhanced ultrasound images according to claim 10, wherein the determining distance information between a microbubble region in the contrast-enhanced ultrasound image and a background region corresponding to the microbubble region comprises:
  performing a binarization processing on the contrast-enhanced ultrasound image based on the microbubble region and the background region to generate a binarized image; and
  determining the distance information between the microbubble region and the background region based on the binarized image.

13. The image processing method based on contrast-enhanced ultrasound images according to claim 9, wherein the microbubble region comprises a plurality of pixel blocks, and the determining distance information between a microbubble region in the contrast-enhanced ultrasound image and a background region corresponding to the microbubble region comprises:
  determining, for each pixel block of the plurality of pixel blocks, a shortest distance from the pixel block to the background region; and
  determining the distance information based on shortest distances respectively corresponding to the plurality of pixel blocks.

14. The image processing method based on contrast-enhanced ultrasound images according to claim 10, wherein the microbubble region comprises a plurality of pixel blocks, and the determining distance information between a microbubble region in the contrast-enhanced ultrasound image and a background region corresponding to the microbubble region comprises:
  determining, for each pixel block of the plurality of pixel blocks, a shortest distance from the pixel block to the background region; and
  determining the distance information based on shortest distances respectively corresponding to the plurality of pixel blocks.

15. The image processing method based on contrast-enhanced ultrasound images according to claim 10, wherein the shortest distance is a Euclidean distance or a Manhattan distance.

16. A non-transitory computer readable storage medium storing a computer program for executing the image processing method based on contrast-enhanced ultrasound images, applied to a first contrast-enhanced ultrasound image sequence comprising microbubbles, comprising:
performing a first decoupling operation on the first contrast-enhanced ultrasound image sequence to generate a second contrast-enhanced ultrasound image sequence corresponding to the first contrast-enhanced ultrasound image sequence, the first decoupling operation being used to improve spatial sparsity of the microbubbles; and
performing a second decoupling operation on the second contrast-enhanced ultrasound image sequence to generate a third contrast-enhanced ultrasound image sequence corresponding to the second contrast-enhanced ultrasound image sequence, the second decoupling operation being used to improve temporal sparsity of the microbubbles;
wherein the performing a second decoupling operation on the second contrast-enhanced ultrasound image sequence to generate a third contrast-enhanced ultrasound image sequence corresponding to the second contrast-enhanced ultrasound image sequence comprises: determining one-dimensional grayscale fluctuation signals corresponding to a plurality of pixel coordinates respectively, based on the plurality of pixel coordinates corresponding to the second contrast-enhanced ultrasound image sequence and pixel value sets corresponding to the plurality of pixel coordinates respectively; and
generating the third contrast-enhanced ultrasound image sequence corresponding to the second contrast-enhanced ultrasound image sequence based on the one-dimensional grayscale fluctuation signals corresponding to the plurality of pixel coordinates respectively;
before the determining one-dimensional grayscale fluctuation signals corresponding to a plurality of pixel coordinates respectively, based on the plurality of pixel coordinates corresponding to the second contrast-enhanced ultrasound image sequence and pixel value sets corresponding to the plurality of pixel coordinates respectively, further comprising:
determining a space coordinate system corresponding to the second contrast-enhanced ultrasound image sequence, the space coordinate system being capable to represent image sequence information; and
determining the plurality of pixel coordinates corresponding to the second contrast-enhanced ultrasound image sequence and the pixel value sets corresponding to the plurality of pixel coordinates respectively, based on the second contrast-enhanced ultrasound image sequence and the spatial coordinate system.

17. An image processing apparatus based on contrast-enhanced ultrasound images, applied to a first contrast-enhanced ultrasound image sequence comprising microbubbles, comprising a memory, a processor, and a computer program stored in the memory and executed by the processor, wherein when the computer program is executed by the processor, the processor implements the following steps:
performing a first decoupling operation on the first contrast-enhanced ultrasound image sequence to generate a second contrast-enhanced ultrasound image sequence corresponding to the first contrast-enhanced ultrasound image sequence, the first decoupling operation being used to improve spatial sparsity of the microbubbles; and
performing a second decoupling operation on the second contrast-enhanced ultrasound image sequence to generate a third contrast-enhanced ultrasound image sequence corresponding to the second contrast-enhanced ultrasound image sequence, the second decoupling operation being used to improve temporal sparsity of the microbubbles;
wherein the performing a second decoupling operation on the second contrast-enhanced ultrasound image sequence to generate a third contrast-enhanced ultrasound image sequence corresponding to the second contrast-enhanced ultrasound image sequence comprises: determining one-dimensional grayscale fluctuation signals corresponding to a plurality of pixel coordinates respectively, based on the plurality of pixel coordinates corresponding to the second contrast-enhanced ultrasound image sequence and pixel value sets corresponding to the plurality of pixel coordinates respectively; and
generating the third contrast-enhanced ultrasound image sequence corresponding to the second contrast-enhanced ultrasound image sequence based on the one-dimensional grayscale fluctuation signals corresponding to the plurality of pixel coordinates respectively:
before the determining one-dimensional grayscale fluctuation signals corresponding to a plurality of pixel coordinates respectively, based on the plurality of pixel coordinates corresponding to the second contrast-enhanced ultrasound image sequence and pixel value sets corresponding to the plurality of pixel coordinates respectively, further comprising:
determining a space coordinate system corresponding to the second contrast-enhanced ultrasound image sequence, the space coordinate system being capable to represent image sequence information; and
determining the plurality of pixel coordinates corresponding to the second contrast-enhanced ultrasound image sequence and the pixel value sets corresponding to the plurality of pixel coordinates respectively, based on the second contrast-enhanced ultrasound image sequence and the spatial coordinate system.

* * * * *